United States Patent [19]

Navarro et al.

[11] Patent Number: 5,534,030
[45] Date of Patent: Jul. 9, 1996

[54] SPINE DISC

[75] Inventors: Richard R. Navarro, Strongsville; Carl R. McMillin, Brecksville; Karl B. Zimmers, Ravenna, all of Ohio

[73] Assignee: AcroMed Corporation, Cleveland, Ohio

[21] Appl. No.: 232,861

[22] Filed: Apr. 25, 1994

Related U.S. Application Data

[63] Continuation of Ser. No. 15,613, Feb. 9, 1993, abandoned.
[51] Int. Cl.⁶ .................................................. A61F 2/44
[52] U.S. Cl. ................................................. 623/17
[58] Field of Search ............................ 623/17, 18, 20, 623/16; 606/61, 62, 63, 64

[56] References Cited

U.S. PATENT DOCUMENTS

| | | |
|---|---|---|
| 2,677,369 | 5/1954 | Knowles . |
| 3,867,728 | 2/1975 | Stubstad et al. ............... 623/17 |
| 4,285,070 | 8/1981 | Averill ........................... 623/20 |
| 4,863,477 | 9/1989 | Monson . |
| 4,944,756 | 7/1990 | Kenna ............................. 623/20 |
| 4,946,378 | 8/1990 | Hirayama et al. ............... 623/17 |
| 5,002,576 | 3/1991 | Fuhrmann et al. .............. 623/17 |
| 5,071,437 | 12/1991 | Steffee .......................... 623/17 |
| 5,171,281 | 12/1992 | Parsons et al. ................ 623/17 |
| 5,306,308 | 4/1994 | Gross et al. ................... 623/17 |

FOREIGN PATENT DOCUMENTS

| | | | |
|---|---|---|---|
| 8707827 | 12/1987 | WIPO . | |
| 9105521 | 5/1991 | WIPO ................ | 623/17 |

Primary Examiner—Debra S. Brittingham
Attorney, Agent, or Firm—Tarolli, Sundheim, Covell, Tummino & Szabo

[57] ABSTRACT

A spinal disc prosthesis comprises an upper rigid plate, a lower rigid plate, and an elastomeric core interposed between the plates and adhered to the plates. The elastomeric core has an upper portion with an outer peripheral surface extending substantially perpendicular to the upper plate. A lower portion of the elastomeric core has an outer peripheral surface extending substantially perpendicular to the lower plate. An intermediate portion of the elastomeric core, extending between the upper and lower portions, has a concave outer peripheral surface. Each of the upper and lower plates has a plurality of ribs extending into the elastomeric core to secure the elastomeric core to the upper and lower plates.

18 Claims, 4 Drawing Sheets

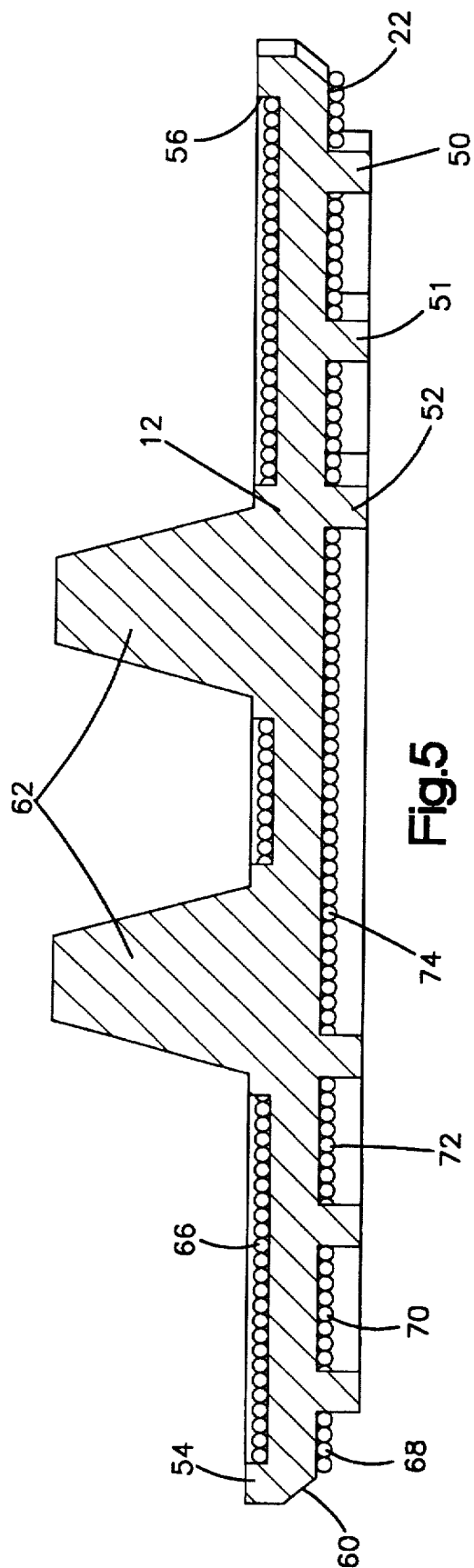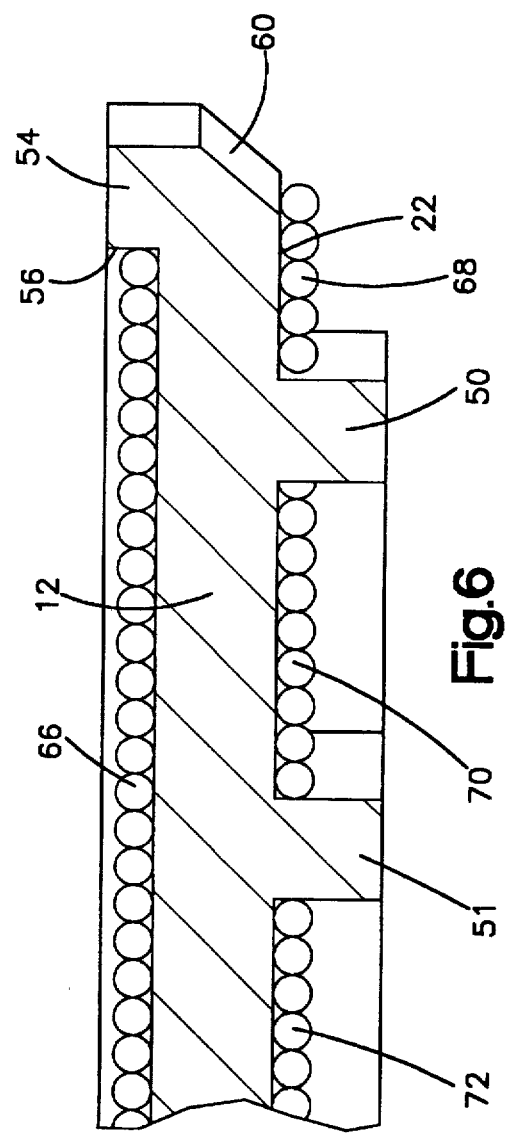

SPINE DISC

This is a continuation of application Ser. No. 08/015,613 filed on Feb. 9, 1993, now abandoned.

BACKGROUND OF THE INVENTION

The present invention relates to an artificial spinal disc prosthesis to replace a damaged or degenerated spinal disc.

A known spinal disc prosthesis is disclosed in U.S. Pat. No. 3,867,728. U.S. Pat. No. 3,867,728 discloses a spinal disc prosthesis which in one form comprises a single piece of elastomer molded to have a concave outer peripheral surface. The elastomer is interposed between and adhered to two outer covering elements. The concave outer peripheral surface extends from one of the covering elements to the other of the covering elements. When a bending moment is applied to the spinal disc prosthesis, the concave peripheral surface of the elastomeric core is stretched along one side. Stresses induced in the disc prosthesis, due to the stretching of the one side of the elastomeric core, are greatest at the interfaces between the elastomeric core and the two covering elements. Therefore, the covering elements could possibly separate from the elastomeric core.

U.S. Pat. No. 5,071,437 discloses a spinal disc prosthesis comprising an upper flat rigid plate, a lower flat rigid plate and a flat elastomeric core interposed between the plates and adhered to the plates. A porous coating is provided on the plates adjacent to the elastomeric core to secure the plates to the elastomeric core. When a crack forms between one of the plates and the elastomeric core, the crack may propagate across the interface between the plate and the elastomeric core causing the plate to separate from the elastomeric core.

SUMMARY OF THE INVENTION

The present invention provides a new and improved spinal disc prosthesis to replace a damaged spinal disc. The spinal disc prosthesis of the present invention comprises an upper rigid plate, a lower rigid plate, and an elastomeric core interposed between the plates and adhered to the plates. The elastomeric core has an upper portion extending from the upper plate. The upper portion of the elastomeric core has an outer peripheral surface extending substantially perpendicular to the upper plate. A lower portion of the elastomeric core extends from the lower plate and has an outer peripheral surface extending substantially perpendicular to the lower plate. An intermediate portion of the core extends between the upper and lower portions and has a concave outer peripheral surface. When a bending moment and/or a translational force is applied to the spinal disc prosthesis, the stresses due to the stretching of one side of the concave surface are reduced at the intersection of the plates and core compared to a core having straight peripheral sides. The concave outer peripheral surface intersects the outer peripheral surfaces of the upper and lower portions of the core in the body of the core and not at the interfaces of the core with the upper and lower plates. Thus, the upper and lower plates have less tendency to separate from the elastomeric core.

Each of the upper and lower plates includes at least one rib extending into (embedded in) and adhered to the elastomeric core. Preferably, each of the plates includes a plurality of concentric ribs extending into the core that have substantially the same shape as an outer peripheral surface of the plates. Thus, the ribs on a plate are concentric with the outer peripheral surface of the plate. The ribs also reduce the tendency of the plates and core to separate. For example, if a crack is formed between one of the plates and the core, the crack, if it propagates across the interface between the plate and core, must change direction upon reaching a rib. This further minimizes the possibility of separation of the plate and the core.

BRIEF DESCRIPTION OF THE DRAWINGS

The foregoing and other features of the present invention will become more apparent to one skilled in the art upon reading the following description of a preferred embodiment with reference to the accompanying drawings, wherein:

FIG. 5 is a sectional view of the plate of FIG. 4 taken along the line 5—5 of FIG. 4;

FIG. 6 is an enlarged sectional view of a portion of the plate of FIG. 5; and

DESCRIPTION OF PREFERRED EMBODIMENT

Figure 2:
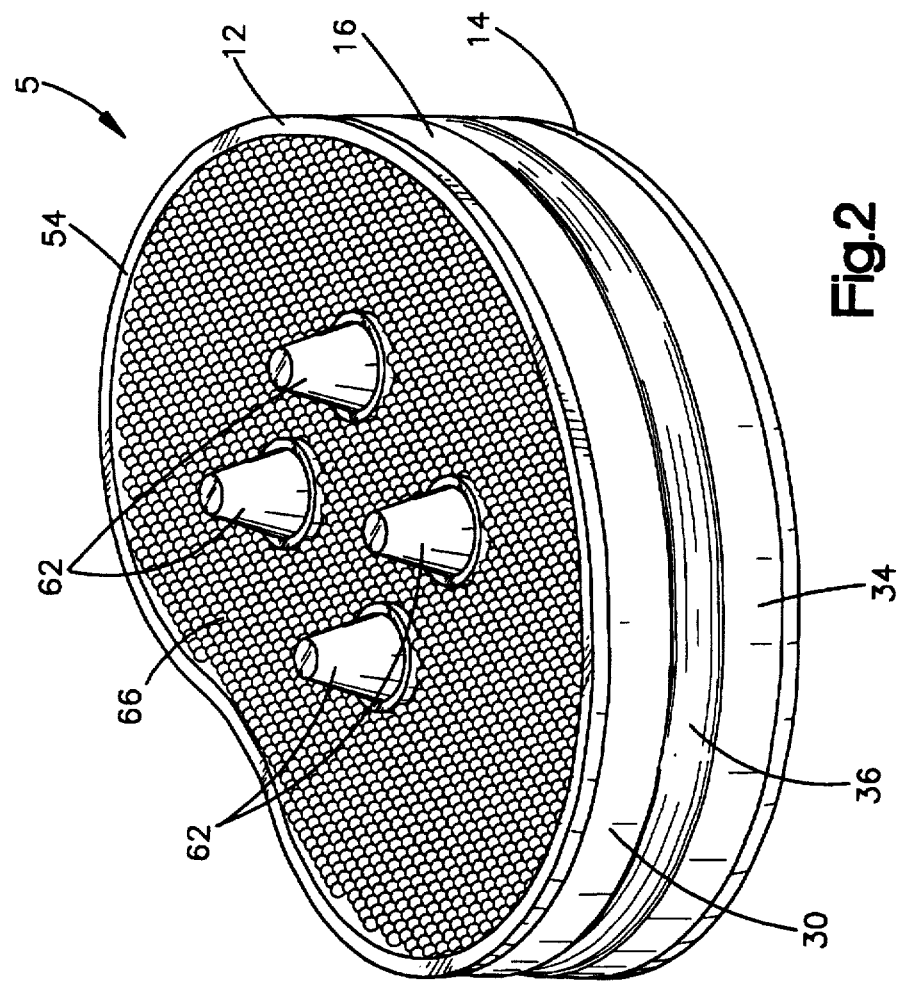
FIG. 2 is a perspective view of the artificial spinal disc of FIG. 1.
Figure 1:
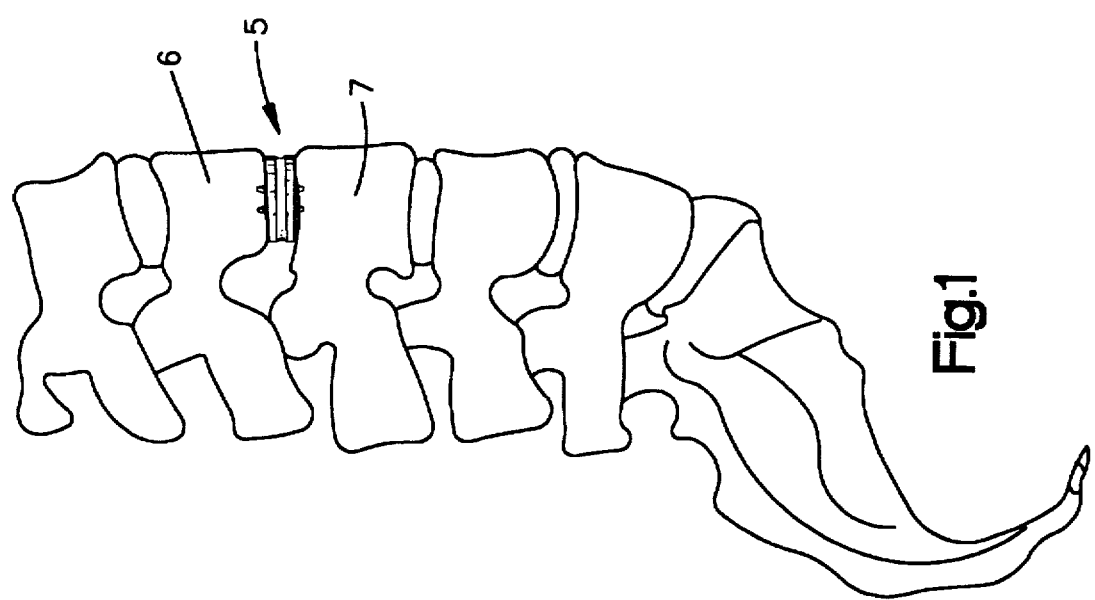
FIG. 1 is an elevation view of a human spinal column having an artificial disc in accordance with that of the present invention placed therein.
Figure 3:
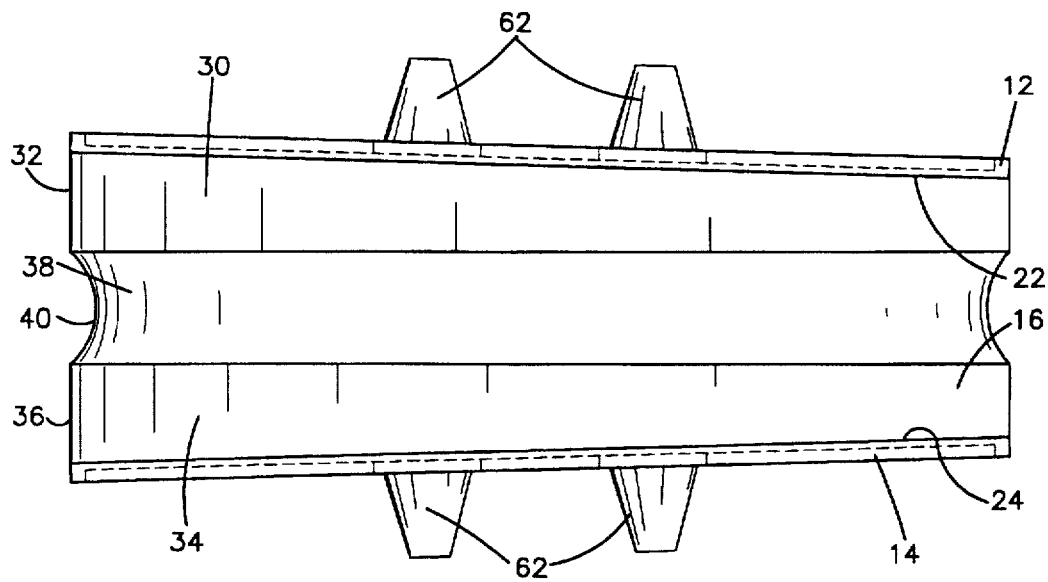
FIG. 3 on the same sheet of drawings as FIG. 7 is an elevational view of the spinal disc of FIG. 2.

A spinal disc prosthesis 5 (FIG. 1) is located between upper and lower vertebrae 6, 7 of a human spine. The disc 5 comprises an upper rigid plate 12, a lower rigid plate 14, and an elastomeric core 16 interposed between the two rigid plates 12, 14 and adhered to the two plates (FIGS. 2 and 3). The upper plate 12 includes a surface 22 (FIG. 3) adhered to the core 16 and the lower plate 14 includes a surface 24 adhered to the core. The surface 22 of the plate 12 lies in a first plane which extends at an angle of approximately 3° to a second plane in which the surface 24 lies. Thus, the disc 5 and core 16 have a wedge shape. However, it is contemplated that the core 16 may be of uniform thickness and thus the rigid plates 12 and 14 would be parallel to each other.

The core 16 comprises an upper portion 30 extending from the upper plate 12. The thickness of the upper portion 30 is substantially larger than the thickness of each of the plates 12, 14. The upper portion 30 has an outer peripheral surface 32 extending substantially perpendicular to the upper plate 12. The core 16 also includes a lower portion 34 with a thickness substantially larger than the thickness of each of the plates 12, 14 and equal to the thickness of the upper portion 30. The lower portion 34 of the core 16 has an outer peripheral surface 36 extending substantially perpendicular to the lower plate 14. An intermediate portion 38 of the core 16 extends between the upper portion 30 and the lower portion 34. The intermediate portion 38 has a concave outer peripheral surface 40 defining a groove extending around the core 16 and located between the upper portion 30 and lower portion 34.

Of the total thickness of the elastomeric core 16, the upper portion 30 is slightly less than 33% and about 31%, the lower portion 34 is also slightly less than 33% and about 31%, and the intermediate portion 38 is slightly more than 33% and about 38%. Also, since the core 16 is wedge shaped the lower portion 34, and the upper portion 30 are wedge shaped, i.e. vary in thickness as they extend from one side of the disc 5 to the other. The intermediate portion 38 is of substantially uniform thickness. Since the intermediate portion is of uniform thickness and the core 16 is wedge shaped, the intermediate portion is a greater percentage of the thickness of the core on the posterior side of the disc 5 than on the anterior side of the disc 5.

Figure 4:
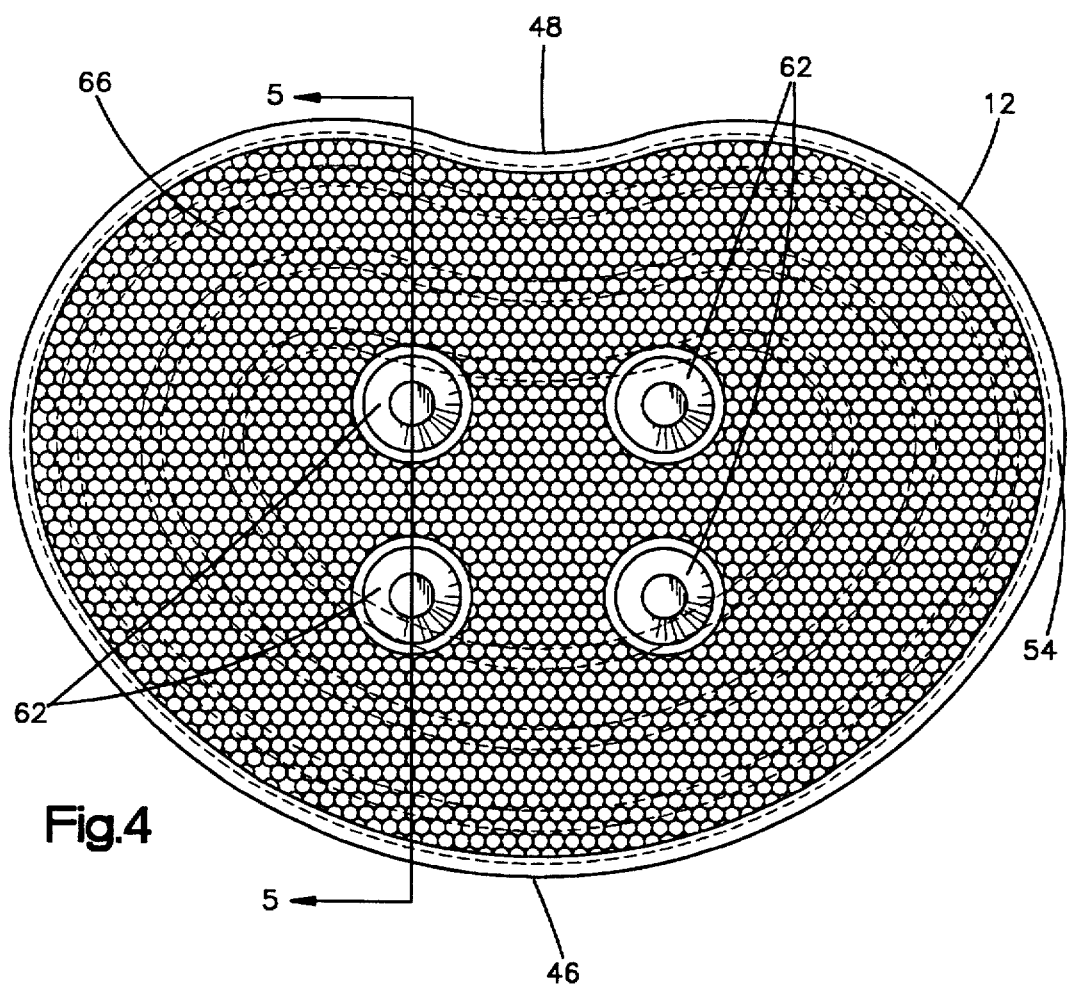
FIG. 4 is a plan view of a plate which is a part of the spinal disc of FIG. 3.

The plates 12 and 14 are identical and therefore only plate 12 will be described. The plate 12 is preferably kidney shaped in plan view with a curved convex side 46 (FIG. 4) and an opposed concave side 48. The configuration shown in FIG. 4 is designed to conform generally to the shape of a natural human spinal disc. The dimensions of the core 16 in plan view are identical to the dimensions of the plates 12 and 14 in plan view. Thus, the rigid plates 12 and 14 and core 16 completely overly each other, and the rigid plates 12 and 14 do not extend beyond the core 16 nor does the core 16 extend beyond the rigid plates 12, 14.

Figure 7:
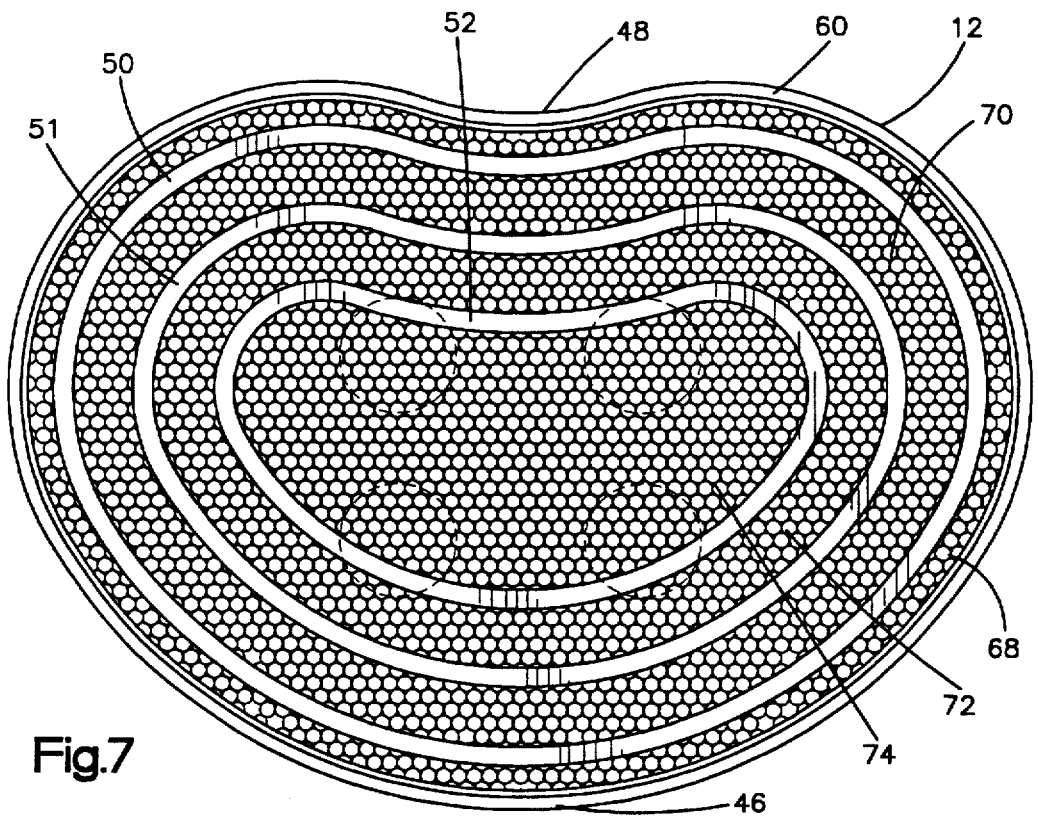
FIG. 7 (on the second sheet of drawings) is a plan view of the bottom of the plate of FIG. 4.

The plate 12 includes a plurality of concentric kidney shaped ribs 50, 51 and 52 (FIGS. 5–7). Preferably, each of the plates 12, 14 includes three ribs 50, 51 and 52. The ribs 50, 51 and 52 are also concentric with the outer peripheral surface of the plate 12.

The rib 50 extends from the plate 12 near the outer peripheral surface of the plate. The rib 52 extends from the plate 12 relatively close to the center of the plate and the rib 51 extends from the plate in an area between ribs 50 and 52. The distance between the ribs 50 and 51 is equivalent to the distance between the ribs 51 and 52. The ribs 50, 51 and 52 extend into the core 16 and are adhered to the core to assist in securing the plates 12 and 14 to the core. A rib 54 (FIG. 5) on the outer periphery of plate 12 extends away from the core 16 and defines a recess 56 in the side of plate 12 opposite the side from which the ribs 50, 51 and 52 extend. The plate 12 includes a chamfer 60 along the outer periphery of the plate. The core 16 covers the chamfer 60 (shown in FIG. 6).

Both the upper and lower plates 12, 14 have, on their exposed faces, a plurality of conical projections 62 which are spaced apart and extend vertically outwardly from the plates. The projections 62 are adapted to fit within seats or depressions in the opposed vertebrae 6, 7. The projections 62 position the disc 5 relative to the vertebrae 6, 7 and function to maintain that position.

The recess 56 receives a porous coating 66. Also, the inner surface 22 of the plate is covered with porous coatings 68, 70, 72, and 74. The porous coating 68 lies between the rib 50 and the outer periphery of the plate 12. The porous coating 70 lies between ribs 50 and 51, and the porous coating 72 lies between ribs 51 and 52. The porous coating 74 lies within the rib 52 and is surrounded by the rib 52. The ribs 50, 51 and 52 are not covered by a porous coating.

The rib 54, defining the recess 56 for receiving the porous coating 66, extends outwardly from the plate 12 a distance slightly greater than the distance the porous coating 66 extends from the plate, see FIGS. 5 and 6. The ribs 50, 51 and 52 extend from the plate 12 a distance substantially greater than the distance the porous coatings 68-74 extend from the plate. Thus, the ribs 50, 51 and 52 extend into the core 16 a substantial distance to secure the plates 12 and 14 to the core.

The porous coatings 66–74 comprise a layer of small spherical particles. The spherical particles are preferably made of commercially pure titanium, but could be made of any suitable biocompatible material. The spherical particles are sized such that none of the spherical particles pass through a 25 mesh U.S. Series Sieve and all the spherical particles pass through a 40 mesh U.S. Series Sieve. Particles can be applied to the plates by vapor deposition, by plasma jet spraying, by sintering or by any other suitable technique. The coatings 66–74 are firmly adhered to the plates 12, 14 and incapable of removal by normal abrasions. The porous coating 66 provides for ingrowth of tissue to cause the bone to more firmly attach to the plates 12, 14 than if the coating 66 was not present. The coatings 68–74 interlock with the material of the core 16 to provide a strong bond between the plates 12 and 14 and the core 16.

In a preferred embodiment of the present invention, the elastomeric core is made of a composite of 70% by weight of H.P. 100 4099 silicone elastomer and 30% by weight of H.P. 100 4106 silicone elastomer, both manufactured by Dow Corning. The hardness of the H.P. 100 4099 elastomer is between 52 and 60 and the hardness of the H.P. 100 4106 elastomer is between 65 and 75 using the ASTM D2240-86 testing method. The ultimate tensile strength of the H.P. 100 4099 elastomer is greater than 1100 psi and the ultimate tensile strength of the H.P. 100 4106 elastomer is greater than 1,000 psi and each of the silicone elastomers has an ultimate elongation greater than 500% using the ASTM D412-87 testing method. Each of the silicone elastomers has a tear resistance greater than 250 ppi using the ASTM D624-86 testing method. Although the elastomeric core 16 is disclosed as being made of a composite of H.P. 100 4099 and H.P. 100 4106 it can be made of any elastomeric material that provides the characteristics of a natural disc.

The plates 12 and 14 are preferably made of a biocompatible metal such as a titanium-vanadium-aluminum alloy having about 90% by weight titanium, about 6% by weight aluminum and about 4% by weight vanadium. Although the plates 12, 14 are disclosed as being made out of a titanium-vanadium-aluminum alloy they can be made out of any suitable biocompatible material including but not limited to a composite plastic material and the like.

The plates 12 and 14 are milled out of a block of metal. However, the plates 12 and 14 could be otherwise manufactured, for example, they could be cast. The spherical particles forming the porous coatings 66–74 are placed on the plates and preferably sintered to the plates 12 and 14 by placing the plate with the particles in place in a heated oven to secure the particles to the plates.

To construct the prosthesis 5, the plates 12 and 14, with the coatings 66–74 in place, are cleaned in a methyl ethyl ketone or similar reagent bath for approximately 25 minutes. The plates are then cleaned with an alkaline cleaning solution and rinsed in distilled water. Then they are dipped in an acid solution such as sulfuric acid pickling solution and rinsed in distilled water. Then the plates are etched for example with a nitric hydrofluoric acid solution to remove any oxide coating from the plates. They are then rinsed in distilled water, and a primer such as about a 5% solution of DC-1107 in heptane/methylene chloride is applied to all surfaces of the plates that will be bonded to the core 16. The primer is applied within about 2 hours. The DC-1107 is manufactured by Dow Corning. The plates are then placed in a mold and the elastomeric material is flowed into the mold and adhered to the ribs 50, 51, 52 and coatings 68, 70, 72, 74. The elastomer is then cured.

When a bending moment and/or a translational force is applied to the spinal disc 5, the stresses due to the stretching of one side of the concave surface 40 are reduced at the intersection between the core and plates compared to a straight sided peripheral core. Thus, the plates have less tendency to separate from the elastomeric core.

Also, if a crack is formed between one of the plates 12, 14 and the core 16, the crack must change direction upon reaching one of the ribs 50, 51 and 52 if the crack propagates across the interface between the plate and the core. Such a change in direction is less likely to occur than the crack continuing to propagate in the absence of the ribs. Therefore, the possibility of the plates 12, 14 separating from the core 16 is minimized.

From the above description of the invention, those skilled in the art will perceive improvements, changes and modifications. Such improvements, changes and modifications within the skill of the art are intended to be covered by the appended claims.

Having described the invention, the following is claimed:

1. A spinal disc prosthesis to replace a damaged spinal disc comprising:

an upper rigid plate;

a lower rigid plate;

an elastomeric core interposed between said plates and adhered to said plates, said elastomeric core comprising an upper portion extending from said upper plate toward said lower plate, said upper portion of said core having an outer peripheral surface extending from said upper plate and substantially perpendicular to said upper plate, a lower portion extending from said lower plate toward said upper plate, said lower portion of said core having an outer peripheral surface extending from said lower plate and substantially perpendicular to said lower plate, and an intermediate portion extending between said upper and lower portions, said intermediate portion having a concave outer peripheral surface extending between said outer peripheral surfaces of said upper and lower portions of said core and defining a groove extending around said core and located between said upper and lower portions of said core.

2. A spinal disc prosthesis as defined in claim 1 wherein each of said upper and lower portions of said core has a thickness which is substantially larger than a thickness of each of said plates.

3. A spinal disc prosthesis as defined in claim 1 wherein said upper plate has a lower side surface lying in a first plane and said lower plate has an upper side surface lying in a second plane, said first plane extending at an acute angle to said second plane.

4. A spinal disc prosthesis as defined in claim 3 wherein said first plane extends at an angle of approximately 3° to said second plane.

5. A spinal disc prosthesis as defined in claim 1 wherein each of said plates includes at least one rib adhered to and extending into said elastomeric core.

6. A spinal disc prosthesis as defined in claim 5 wherein each of said plates includes a plurality of ribs extending into said elastomeric core.

7. A spinal disc prosthesis to replace a damaged disc comprising:

an upper rigid plate;

a lower rigid plate;

a resilient elastomeric core interposed between said plates and adhered to said plates; and each of said upper and lower plates having a surface facing toward said resilient elastomeric core and including at least one rib extending along said surface, said rib having a thickness measured from said plate toward said resilient elastomeric core and a length measured along said surface of said plate, the length of said rib being greater than the thickness of said rib, said rib being adhered to and extending into said resilient elastomeric core to resist separation of said plates and core.

8. A spinal disc prosthesis as defined in claim 7 wherein each of said plates includes a plurality of ribs adhered to and extending into said elastomeric core.

9. A spinal disc prosthesis as defined in claim 7 wherein each of said plates includes a rib extending outwardly away from said elastomeric core, said outwardly extending rib defining a recess and a porous particle coating on said plates and located in said recess.

10. A spinal disc prosthesis as defined in claim 7 wherein said elastomeric core comprises an upper portion extending from said upper plate, said upper portion of said core having an outer peripheral surface extending substantially perpendicular to said upper plate, a lower portion extending from said lower plate, said lower portion of said core having an outer peripheral surface extending substantially perpendicular to said lower plate, and an intermediate portion extending between said first and second portions, said intermediate portion having a concave outer peripheral surface.

11. A spinal disc prosthesis as defined in claim 10 wherein said upper portion is about 31% of a thickness of said core, said lower portion is about 31% of the thickness of said core, and said intermediate portion is about 38% of the thickness of said core.

12. A spinal disc prosthesis to replace a damaged spinal disc comprising:

an upper rigid plate;

a lower rigid plate; and an elastomeric core interposed between said plates and adhered to said plates, said elastomeric core comprising an upper portion extending from said upper plate toward said lower plate, said upper portion of said core having an outer peripheral surface extending substantially perpendicular to said upper plate, a lower portion extending from said lower plate toward said upper plate, said lower portion of said core having an outer peripheral surface extending substantially perpendicular to said lower plate, and an intermediate portion extending between said upper and lower portions, said intermediate portion having a concave outer peripheral surface extending between said outer peripheral surfaces of said upper and lower portions of said core and defining a groove extending around said core and located between said upper and lower portions of said core;

each of said plates including at least one rib adhered to and extending into said elastomeric core, said plate having an outer peripheral surface with a shape, said rib having substantially the same shape as said outer peripheral surface of said plate.

13. A spinal disc prosthesis to replace a damaged disc comprising:

an upper rigid plate;

a lower rigid plate;

a resilient elastomeric core interposed between said plates and adhered to said plates; and each of said upper and lower plates having a surface facing toward said resilient elastomeric core and including at least one rib extending along said surface, said rib having a thickness measured from said plate toward said resilient elastomeric core and a length measured along said surface of said plate, the length of said rib being greater than the thickness of said rib, said rib being adhered to and extending into said resilient elastomeric core to resist separation of said plates and core;

said plate having an outer peripheral surface with a shape, said rib having substantially the same shape as said outer peripheral surface of said plate.

14. A spinal disc prosthesis as defined in claim 13 wherein said plate and said core are kidney shaped.

15. A spinal disc prosthesis to replace a damaged disc comprising:

an upper rigid plate;

a lower rigid plate;

a resilient elastomeric core interposed between said plates and adhered to said plates; and each of said upper and lower plates having a surface facing toward said resilient elastomeric core and including a plurality of ribs extending along said surface, said ribs having a thickness measured from said plate toward said resilient elastomeric core and a length measured along said surface of said plate, the length of said ribs being greater than the thickness of said ribs, said ribs being adhered to and extending into said resilient elastomeric core to resist separation of said plates and core;

said plate having an outer peripheral surface with a shape, said plurality of ribs being concentric and having substantially the same shape as said outer peripheral surface of said plate.

16. A spinal disc prosthesis to replace a damaged spinal disc comprising:

an upper rigid plate;

a lower rigid plate;

an elastomeric core interposed between said plates and adhered to said plates, said elastomeric core comprising an upper portion extending from said upper plate toward said lower plate, said upper portion of said core having an outer peripheral surface with a substantial portion extending substantially perpendicular to said upper plate, a lower portion extending from said lower plate toward said upper plate, said lower portion of said core having an outer peripheral surface with a substantial portion extending substantially perpendicular to said lower plate, and an intermediate portion extending between said upper and lower portions, said intermediate portion having a concave outer peripheral surface extending between said outer peripheral surfaces of said upper and lower portions of said core and defining a groove extending around said core and located between said upper and lower portions of said core.

17. A spinal disc prosthesis as defined in claim 16 wherein said outer peripheral surface of said upper portion of said core extends perpendicular to said upper plate at an intersection of said outer peripheral surface of said upper portion with said upper plate, said outer peripheral surface of said lower portion extending perpendicular to said lower plate at an intersection of said outer peripheral surface of said lower portion with said lower plate.

18. A spinal disc prosthesis as defined in claim 16 wherein each of said plates includes a plurality of ribs adhered to and extending into said elastomeric core.

\* \* \* \* \*

UNITED STATES PATENT AND TRADEMARK OFFICE
CERTIFICATE OF CORRECTION

PATENT NO. : 5,534,030
DATED : July 9, 1996
INVENTOR(S) : Richard R. Navarro, Carl R. McMillin and Kari B. Zimmers It is certified that error appears in the above-indentified patent and that said Letters Patent is hereby corrected as shown below:

Cover Page, item [75], Inventors: change "Karl B. Zimmers" to --Kari B. Zimmers--

Signed and Sealed this

Tenth Day of December, 1996

Attest:

*Attesting Officer*

BRUCE LEHMAN

*Commissioner of Patents and Trademarks*